United States Patent [19]
Piety et al.

[11] Patent Number: 5,637,871
[45] Date of Patent: Jun. 10, 1997

[54] PORTABLE DIGITAL INFRARED THERMOGRAPHY SYSTEM

[75] Inventors: Kenneth R. Piety; Terry G. Carpenter; Rexford A. Battenberg, all of Knoxville, Tenn.

[73] Assignee: Computational Systems, Inc., Knoxville, Tenn.

[21] Appl. No.: 486,763

[22] Filed: Jun. 7, 1995

Related U.S. Application Data

[63] Continuation-in-part of Ser. No. 378,796, Jan. 26, 1995, abandoned, which is a continuation of Ser. No. 73,132, Jun. 7, 1993, Pat. No. 5,386,117.

[51] Int. Cl.$^6$ .................................................. G01N 25/72
[52] U.S. Cl. .......................... 250/330; 250/358.1
[58] Field of Search .................................. 250/330, 332, 250/334, 358.1

[56] References Cited

U.S. PATENT DOCUMENTS

| 3,531,642 | 9/1970 | Barnes et al. . |
| 3,854,336 | 12/1974 | Bibby . |
| 4,379,461 | 4/1983 | Nilsson et al. . |
| 4,524,386 | 6/1985 | Scott . |
| 4,539,588 | 9/1985 | Areissohn et al. . |
| 4,671,674 | 6/1987 | Detronde . |
| 4,687,344 | 8/1987 | Lillquist . |
| 4,695,881 | 9/1987 | Kennedy et al. . |

(List continued on next page.)

FOREIGN PATENT DOCUMENTS

| 59-115686 | 7/1984 | Japan . |
| 63-175735 | 7/1988 | Japan . |

OTHER PUBLICATIONS

Proskurnicki et al., "Mobile Diagnostics of Electrical Systems Using Expert–System Based Thermal Analysis Software", SPIE, vol. 934, Thermosense X, 1988, pp. 149–154.

Cross, et al., "Measurement of Aircraft Surface Temperatures with an Infrared Television System," Proceedings of SPIE 14th Annual Technical Symposium: Photo–Optical Inst. App. & Theory, San Francisco, California, Aug. 1969, pp. 59–65.
Freund, "Infrared Scanning Added to Routine Maintenance," Exergen Corp., EC&M, Oct. 1987, pp. 67–70.
Mikron Advertisement, Oct. 1990.
Sales Brochure—700 Series by Inframetrics (No Date).
Sales Brochure—Thermovision 470 by Agema (No Date).

*Primary Examiner*—Edward J. Glick
*Attorney, Agent, or Firm*—Luedeka, Neely & Graham, P.C.

[57] ABSTRACT

A highly portable infrared thermography system automates the collection, display, analysis, annotation, and recording of thermographic data and facilitates the efficient generation of reports. The system includes an infrared camera and a digital video data collector (VDC) having an embedded PC with an internal hard drive. The VDC also includes a VGA color LCD display with touch screen overlay for displaying images, presenting information to a thermographer, and for receiving data and command inputs from the thermographer. The system can be carried with a custom vest and battery belt, or it can be mounted to a hand truck. Thermographic images captured by the infrared camera are received by the VDC and displayed in real time at rates of at least thirty frames per second to eliminate flicker. The VDC also interfaces with a videotape recorder for displaying and recording images. Other interfaces include a visible image camera interface, a digital video interface, and a base station computer interface. Images of interest are stored on the VDC's hard drive where they can be retrieved for analysis and report generation in the field. A portable printer can be attached to the VDC to enable the thermographer to print reports as they are generated. Images can be annotated by the thermographer on the display, and the annotated images stored. The display is operable to prompt the thermographer with route information regarding particular equipment to be thermograhically inspected, and to suggest particular problems possibly indicated by a particular thermographically-observed condition.

40 Claims, 5 Drawing Sheets

U.S. PATENT DOCUMENTS

| | | |
|---|---|---|
| 4,724,482 | 2/1988 | Duvent .................................. 250/334 X |
| 4,733,079 | 3/1988 | Adams et al. . |
| 4,814,870 | 3/1989 | Crall . |
| 4,849,885 | 7/1989 | Stillwagon et al. . |
| 4,854,724 | 8/1989 | Adams et al. . |
| 4,910,593 | 3/1990 | Weil . |
| 5,045,937 | 9/1991 | Myrick . |
| 5,159,198 | 10/1992 | Kohsaka et al. . |
| 5,292,195 | 3/1994 | Crisman, Jr. . |

PORTABLE DIGITAL INFRARED THERMOGRAPHY SYSTEM

TECHNICAL FIELD

This is a continuation in part of application Ser. No. 08/378,796 filed Jan. 26, 1995, now abandoned, which is a continuation of application Ser. No. 08/073,132 filed Jun. 7, 1993, which issued as U.S. Pat. No. 5,386,117 on Jan. 31, 1995.

The present invention relates generally to the art of infrared thermography. More particularly, it relates to a highly portable system which facilitates the collection, display, analysis, annotation, and recordation of data by a thermographer, the efficient preparation of reports, and the archiving of records relating to thermographic inspection.

BACKGROUND OF THE INVENTION

Infrared thermography, whereby infrared cameras are employed to capture infrared images at any one of several infrared wavelength ranges, is known to be a useful tool in a wide variety of applications. An observed anomaly or problem is known as a thermographic "event" to be reported and possibly diagnosed. The invention is disclosed herein in the context of industrial plant maintenance, also known as preventative maintenance or predictive maintenance. Infrared thermography is also useful in a variety of applications other than plant maintenance, such as EPA studies, agriculture, medical technology, law enforcement, veterinary medicine and military uses.

As one example of a plant maintenance application, an infrared image of the interior of a three-phase electric motor switch box may reveal that one fuse out of three, or the fuse connectors, is hotter than the other two, indicating a potential problem to be corrected before an actual failure occurs.

As another example, within a three-phase electrical control box, a conductor associated with one of the phases may be colder than corresponding conductors associated with the other two phases, indicating that less current is being carried, and pointing to a potential problem to be investigated.

As other examples, within the exemplary context of industrial plant maintenance, the following components may advantageously be inspected employing infrared thermography: transformers, transformer control cubicles, motor control centers, transmission lines, electric motors, steam traps, pipes, valves, belts, components subject to vacuum leaks, insulation in general, roofs and roof insulation, dry type transformers, rotary kilns, auxiliary transformers, start up transformers, distribution panel circuit breakers, relays and ground straps.

A large, heavy, bulky thermographic unit can be difficult, if not impossible, to use in many industrial settings. Plant designs are simply inhospitable to the thermographer who is trying to transport his equipment from one measuring location to another. Therefore, portability is a desirable quality in many infrared thermography applications. Another desirable quality is user friendliness and simplicity.

One method of attempting to achieve portability in prior art systems utilizes a hand truck, or dolly, onto which the thermography equipment is attached. The hand truck and equipment can then be moved from one location to another with greater ease. However, in many situations these systems are less portable than needed or desired. A hand truck loaded with heavy, sensitive electronics is difficult to transport up and down stairs, through tight areas, around large equipment, etc.

Another attempted solution to portability known in the prior art utilizes a hand-held unit that is transported without the aid of a hand truck. Unfortunately, these systems achieve portability at the cost of capability. By reducing the size and weight normally associated with other prior art thermography systems, the hand-held systems exclude many desirable functional features.

Video display speed, data processing power, and internal databus speed have been major design obstacles for which the prior art has not satisfactorily overcome. Internal databus transfer rates are simply too slow to eliminate video display flicker. To avoid the problem, a few systems have elected not to digitize the video signal generated by the camera and to simply route the video signal to the display in analog format. While this approach generally works well to eliminate flicker, the analog format reduces the data processing capabilities and overall versatility of the system.

Prior art infrared thermography systems have also been labor intensive, physically cumbersome, and relatively inefficient from the viewpoint of enabling a thermographer to rapidly and efficiently generate reports. For example, if a thermographer desired to annotate the video image by adding text or perhaps an arrow to indicate an area of interest, this would have to be done with the assistance of a base station computer, or perhaps by manually annotating a hard copy of an image. It could not be accomplished in the field.

There are known prior art thermography systems which employ infrared cameras connected to a videotape recorder whereby a thermographer can record infrared images of various pieces of equipment and other objects. Later, when the thermographer is preparing a report, the videotape is played until desired images are found, which are displayed on a screen, and then captured for a permanent record, either photographically off of the video screen, or digitally.

Another prior art approach to thermography employs an infrared camera having what is in effect "snapshot" capability whereby a limited number of thermographic images, for example thirty-three images, may be digitally captured to a floppy disk included within the infrared camera, for later review.

Systems presently exist that combine the use of an infrared camera with a visible image camera. An image from either camera may be recorded onto a videotape. As an alternative to the visible image video camera, a conventional photographic snapshot camera may be used. These systems do not permit the thermographer to analyze images and generate reports in the field, but instead, the thermographer must later correlate the stored images for analysis and report generation back at the lab. Although computers have been utilized as an excellent tool for manipulating the images and performing analyses on the data, the process remains generally slow and cumbersome. Usually, the thermographer must spend many hours searching the numerous videotape images, looking for particular thermographic events to analyze and document, correlating images of interest to perhaps a visible image that was taken, and then generating the report.

SUMMARY OF THE INVENTION

In accordance with a preferred embodiment of the present invention, there is disclosed a digital infrared thermography system for producing and recording thermographic images of objects. The system has a portable infrared camera for capturing thermographic images of objects, and the camera produces an electronic signal corresponding to the thermographic image captured. A digital data processing and recording device receives and processes the thermographic image signal produced by the camera to produce a formatted digital signal in the form of a plurality of frames of images. Digital display means receive the formatted digital signal and display the images represented by this signal. There are means for selecting individual frames of the formatted digital signal to produce selected digital frame signals. The selected frames can be annotated while displayed on the digital display means. Digital storage means enable storage of the selected digital frame signals.

An additional feature of the present invention is a high speed path dedicated to routing the formatted digital signal to the digital display means for display of the formatted digital signal. This high speed path enables the signal to be displayed at a rate of at least thirty frames of images per second, thereby eliminating flicker on the display.

Another feature of this preferred embodiment is that the digital data processing and recording device comprises a video digitizer for digitizing and multiplexing the infrared camera's electronic thermographic image signal to produce the formatted digital signals.

As a further feature, the system incorporates a portable visible image camera for capturing visible images of objects. The visible image camera produces an electronic visible image signal corresponding to the captured visible images. The video digitizer receives both the electronic visible image signal and the electronic thermographic image signal and employs an internal multiplexor which allows the user, through software control, to select the desired input for digitizing. The selected input signal will be digitized to produce the formatted digital signals. The system also includes an S-video jack for receiving visible image signals from the visible image camera in S-video format. The data processing and recording device further includes means for receiving and processing image signals produced by either of the cameras in digital format. A data processing and recording device has a digital interface for receiving signals from the cameras in digital format. A programmable logic array within the data processing and recording device is programmable to format the camera's digital image signal for further processing by the data processing and recording device.

The system further includes interface means for interfacing the data processing and recording device to an external computer. The data processing and recording device includes an embedded computer.

To enhance overall portability of the system, a portable battery is used to provide power to the system. Portability is also enhanced by a carrying vest that can be worn by a user to carry at least the data processing and recording device.

In another preferred embodiment, the present invention discloses a portable digital infrared thermography unit for processing, displaying, and recording at least thermographic images as represented by thermographic image signals that are comprised of individual frames of thermographic images produced by an infrared camera. The unit comprises a camera interface for receiving at least the thermographic image signals produced by the infrared camera. A video digitizer multiplexes and digitizes image signals received by the camera interface, producing the formatted digital image signals. Digital display means are provided for receiving at least thermographic images as represented by the formatted digital image signals. A high speed path is dedicated to routing at least the formatted digital image signals to the display means for display of the signals at a rate of at least thirty frames of images per second. Also included are means for selecting individual frames of the formatted digital image signals, producing selected digital frame signals. An internal memory is used for storing the selected digital frame signals. An embedded computer is provided to control the processing and display of the formatted digital image signals, and for controlling the storage of the selected digital frame signals in the memory. A databus interconnects at least the video digitizer, digital display means, means for selecting, and embedded computer.

Another feature of this embodiment is that the camera interface is operable to receive visible image signals produced by a visible image camera. The camera interface is further operable to receive visible image signals in S-video format.

As a further feature, a digital video signal interface is provided for receiving digital video signals. The digital video signals are comprised of individual frames of images and are received at a rate of at least thirty frames of images per second to eliminate flicker when displayed. To convert the digital video signals to a format readily useable by the unit, a programmable logic array is provided. The array produces a formatted digital image signal that is received by the high speed path and routed to the display at a rate of at least thirty frames of images per second.

As a further embodiment of the present invention, there is provided a digital portable infrared thermography system for producing, processing, displaying, storing, and outputting to perheral devices thermographic and visible images of objects. The system comprises a portable infrared camera for capturing thermographic images of objects. The infrared camera produces an electronic thermographic image signal comprising individual frames of thermographic images corresponding to the captured thermographc images. A portable visible image camera is included for capturing visible images of objects. The visible image camera produces an electronic visible images signal comprising individual frames of visible images corresponding to the captured visible images. A video data collector receives, processes, displays, stores, and outputs to peripheral devices the thermographic and visible image signals.

The video data collector comprises a camera interface connected to the infrared and visible image cameras for receiving the thermographic and visible image signals. A video digitizer multiplexes and digitizes the image signals received by the interface, producing formatted digital image signals. A digital video signal interface is provided to receive digital video signals comprised of individual frames of images. A programmable logic array converts the digital video signals to a format readily useable by the data collector to produce formatted image signals. A digital LCD display displays thermographic and visible images as represented by the formatted digital image signals. Also included in the data collector are means for selecting and annotating individual frames of the formatted digital image signals to produce selected digital frame signals. An internal hard drive records the selected digital frame signals. To control the processing and displaying of the formatted digital image signals an embedded computer is provided. The embedded computer also functions to control the receiving, multiplexing, processing, displaying, storing, and outputting of the selected digital frame signals.

Portability is enhanced with the use of a portable battery to provide power to the system. A touch screen display enhances portability by eliminating the need to carry a keyboard and mouse. A carrying vest is provided to support at least the video data collector on a person's body.

BRIEF DESCRIPTION OF THE DRAWINGS

The invention will now be described in further detail with reference to the drawings wherein like reference characters designate like or similar elements throughout the several drawings as follows.

DETAILED DESCRIPTION OF THE PREFERRED EMBODIMENT

Figure 1:
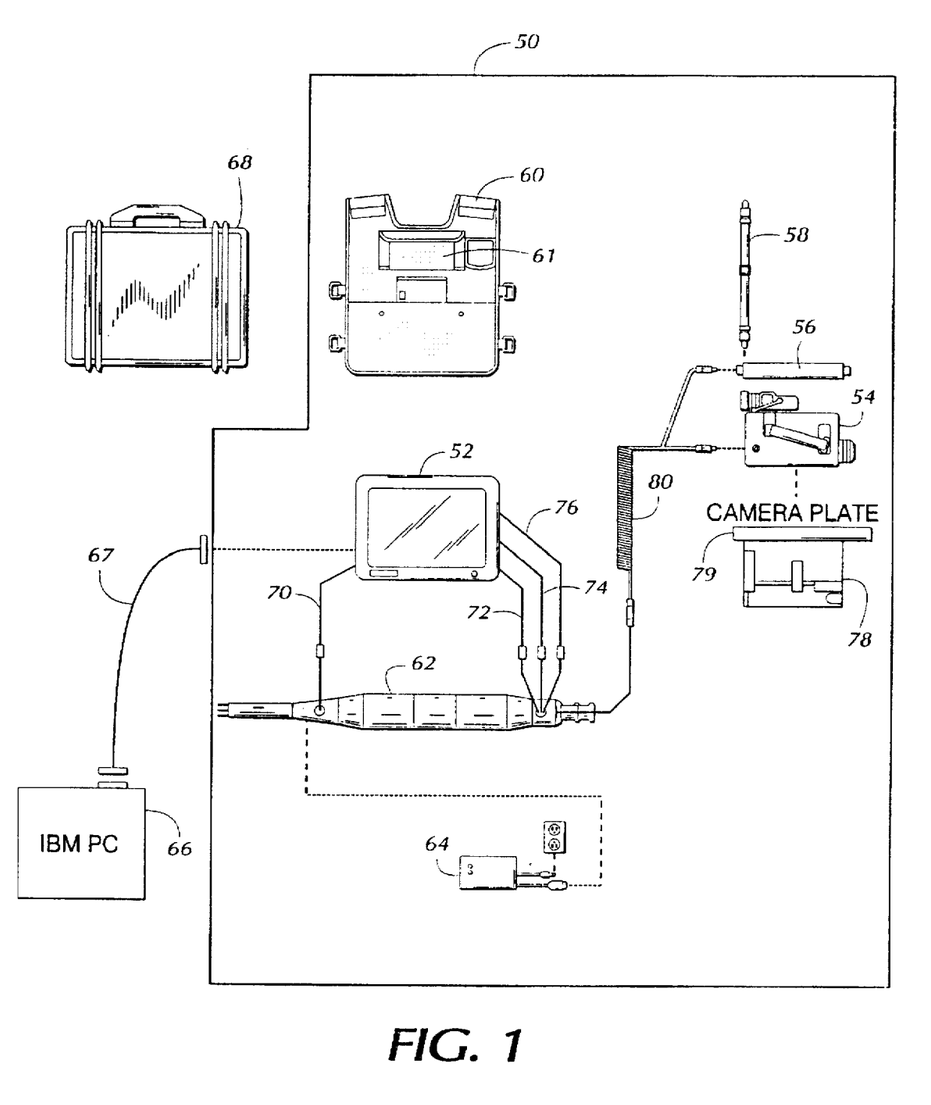
FIG. 1 is a somewhat diagrammatical illustration of an infrared imaging system in accordance with the invention.

FIG. 1 is a somewhat diagrammatical illustration of the infrared imaging system 50 embodying the invention. Video signals representative of thermographic images captured by an infrared camera 54 during thermographic observations are routed to a battery belt 62 via coil cable 80 and then to a video data collector (VDC) 52 via line 72. Thermographic video images captured by an infrared camera 54 are routed to the VDC 52 via line 76. In one embodiment, the infrared camera 54 is suitably mounted to a camera plate 79 which, when rested against the bottom of a camera cradle 78, has a lip edge (not shown) which protrudes beyond the outer edge of the camera cradle 78. Although not required, a visible image camera 56 may be suitably attached to the camera plate 79 for capturing visible spectrum images of the area under thermographic observation. Alternatively, the visible image camera 56 may be stored in a pouch (not shown) that attaches to the battery belt 62 during periods of non-use, thereby eliminating the need for the camera plate 79. The visible video images captured by the visible image camera 56 are similarly routed to the battery belt 62 via coil cable 80 and then to the VDC 52 via line 74 thereby enabling the user, or thermographer, to compare the thermographic image of an area under observation with a visible image of the same area. An optional shoulder strap 58 suitably attached to the camera cradle 79 provides the thermographer with a convenient apparatus for carrying the cameras 54 and 56.

The battery belt 62, which can be worn around the waist of the thermographer, provides the thermographer with a convenient apparatus for carrying electrical power while conducting thermographic inspections in the field. The battery belt 62 also serves to functionally interconnect the infrared and visible image cameras 54 and 56 with the VDC 52, while also supplying power to these components. Power is supplied by the battery belt 62 to the VDC 52 via line 70. In a preferred embodiment, the battery belt 62 is fitted with 12 volt DC rechargeable batteries (not shown) which are used to power the cameras 54 and 56 as well as the VDC 52. Batteries carried within the belt 62 can be recharged with an ordinary battery charger 64.

Any suitable infrared video camera 54 may be employed in the practice of the invention including, by way of example and not limitation, pyroelectric infrared cameras and focal plane array cameras which may include platinum silicide detectors. A typical pyroelectric infrared camera has the characteristics of longwave imaging (8 to 12 micrometers) and good image resolution, with no detector cooling required. A typical focal plane array camera employing a platinum silicide detector has the characteristics of short-wave imaging (2.5 to 5 micrometers) and extremely high image resolution, and includes a built-in battery powered detector cooler. Particular commercially-available infrared cameras which are suitable are the "Pyroviewer" infrared camera and the "Flir" infrared camera.

Likewise, any suitable visible image video camera 56 may be employed. So-called "camcorders" combining a video camera and a video tape recorder are more readily available than are video cameras alone, and it is accordingly advantageous to simply employ the camera portion of a camcorder, while bypassing the recorder portion thereof. A preferred embodiment of the invention employs a small, pen-type camera such as the Sony model XC999 or XC777 camera. This type of camera has the added features of small size and light weight, which are highly desirable features in any portable system. The "pen-type" camera can be suitably attached to the lip edge of the camera plate 79.

With continued reference to FIG. 1, portability of the system 50 is enhanced by use of a customized carrying vest 60, which when worn by the thermographer can be used for hands-off support of the VDC 52. The front of the vest is equipped with a vest cradle 61 sized to receive the VDC 52 so that when the vest is worn, the VDC 52 is conveniently supported by, and easily accessible to, the thermographer. The VDC 52 is preferably equipped with a BOGEN quick disconnect (not shown) for ease of installation in and removal from the vest 60. The quick disconnect enables the user to place the VDC 52 on a desktop stand (not shown) that is capable of tilting the VDC 52 to adjust the viewing angle when the VDC 52 is being used to interface with a base station computer 66.

Figure 2:
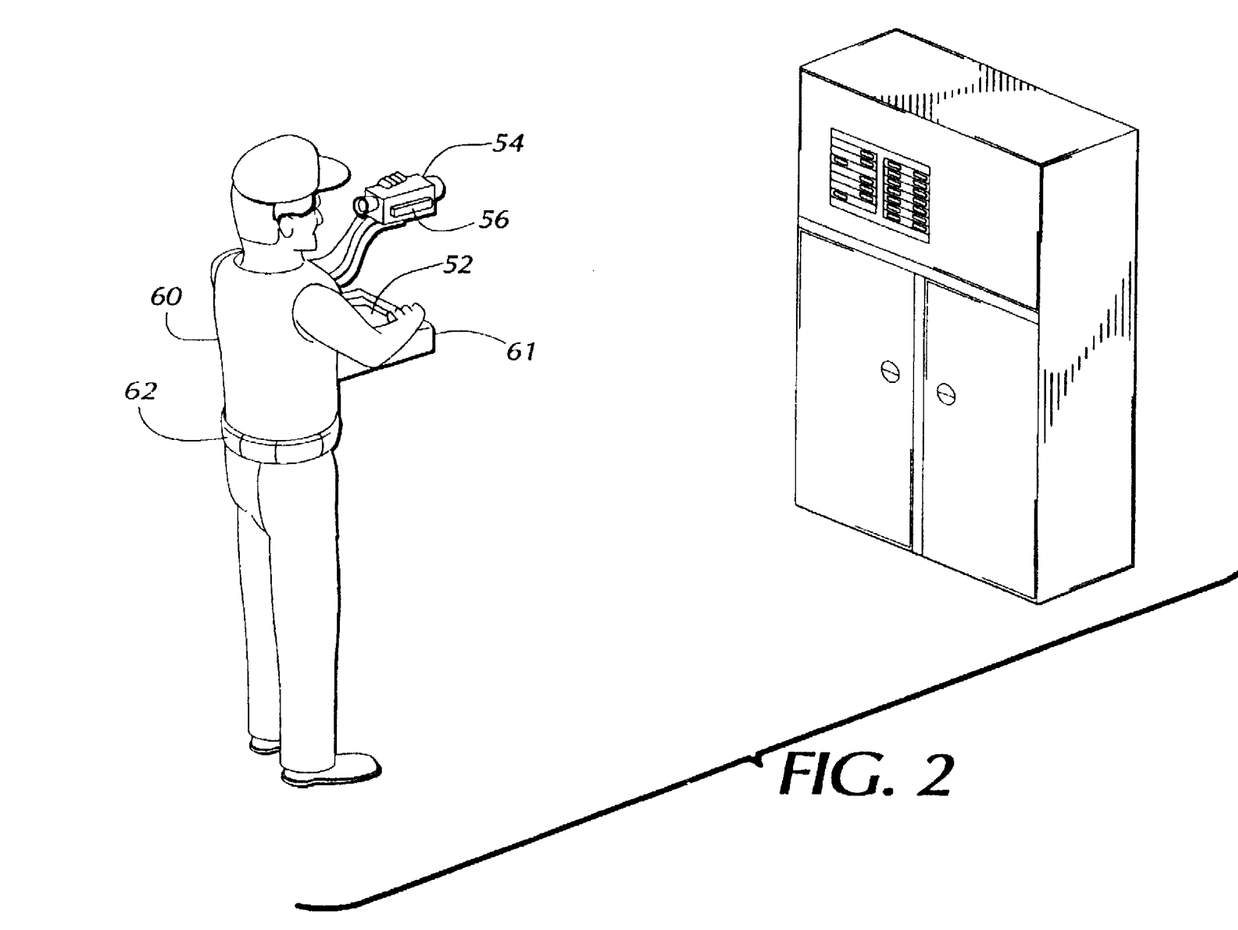
FIG. 2 illustrates a typical use of the invention while conducting thermographic inspections in the field.

FIG. 2 illustrates use of the vest 60 and battery belt 62 while conducting thermographic inspections in the field. It should be noted that although FIG. 2 illustrates a thermographer using the viewfinder of the infrared camera 54, it will be appreciated that the unique capabilities of the VDC 52 enable the thermographer to suspend the camera at his or her side with the use of the carrying strap 58 and "shoot from the hip" while observing the resultant live video on the VDC 52. In this regard, it is not a requirement that either of the cameras 54 and 56 be equipped with a viewfinder.

At this point it will be noted that the VDC 52 is an intelligent device including an embedded personal computer (PC), as will be more fully described. The embedded PC has its own internal hard drive for storing and retrieving data, including infrared and visible images. The VDC 52 is also capable of interfacing with peripheral devices for storing and retrieving images and other data, including interfacing with a base station computer 66.

When not in use, the entire system 50 of FIG. 1 may be transported by means of a convenient carrying case 68. Further, the infrared imaging system can be used as a man-portable device, as previously described, with a hand truck as further described below, or with a portable cart (not shown).

Figure 3:
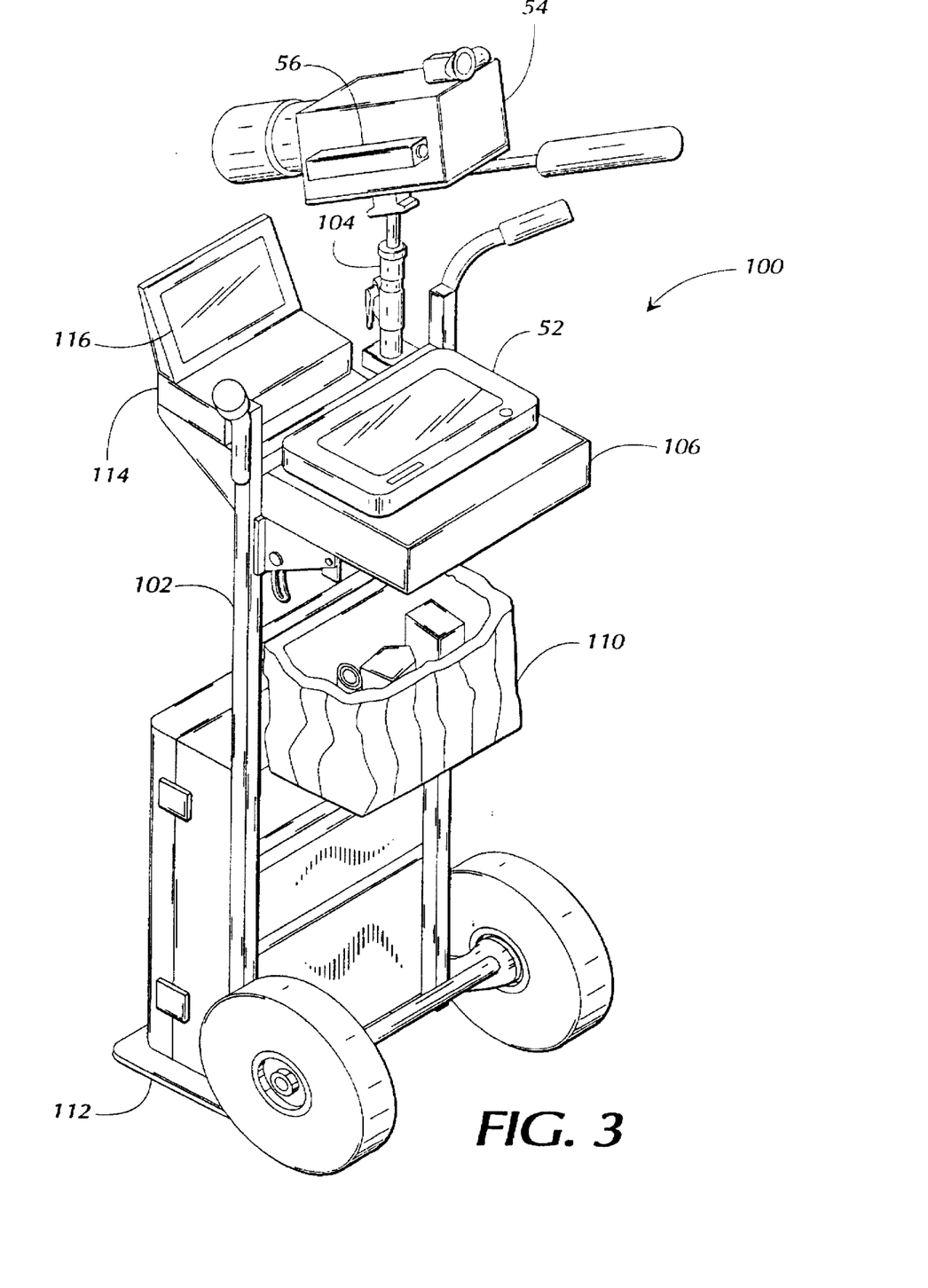
FIG. 3 is a three-dimensional view of the infrared imaging system mounted on a hand truck.

In another preferred embodiment, FIG. 3 provides a three-dimensional view of the infrared imaging system 100 embodying the invention wherein portability is enhanced by means of a hand truck 102. This embodiment is similar to that disclosed in U.S. Pat. No. 5,386,117, which is specifically incorporated herein by reference. Suitably mounted to the hand truck 102 by means of a mount 104 is the infrared camera 54 and the optional visible camera 56 shown in FIG. 1. Although not shown in FIG. 3, the battery belt 62 may be attached at any convenient location on the hand truck 102. A utility pouch 110 provides a suitable location for the battery belt 62. As an alternate source of power, a power interface box 106 is used in place of the battery belt 62 of FIG. 1 to functionally interconnect the infrared and video cameras 54 and 56 and the VDC 52, and to supply power to these components. The power interface box 106 supports the VDC 52 preferably by means of a cutout sized to received the VDC 52. The power interface box 106 preferably derives power from a battery (not shown) which may be included within the power interface box 106 or suitably attached to a lower support plate 112 of the hand truck.

In addition to providing a convenient location for placement of the battery belt 62, the utility pouch 110 of FIG. 3 also affords convenient storage of a variety of items useful to a thermographer, such as, but not limited to, portable instruments for measuring the temperature of a particular point on a piece of equipment, instruments for determining and compensating for emissivity of objects being viewed with the infrared camera 54, remote current-measuring probes, remote temperature-measuring probes, and other remote measurement devices.

As shown in FIG. 3, a videotape recorder 114 may be suitably mounted to the hand truck 102 for recording both infrared and visible images produced by the cameras 54 and 56. Preferably, the videotape recorder 114 also incorporates a monitor screen 116. Presently preferred is a Sony "Walkman" Model No. GV-S50 NTSC Video Recorder/Monitor 116. This particular video recorder/monitor includes a 4 inch×4 inch fold-out color LCD display, and employs "Hi-8 mm" format videotape, with a separate track for recording data and time stamps corresponding to images being recorded. The Sony "GV-S50" video recorder/monitor 116 is an intelligent device, and has a bi-directional control interface implementing LANC technology as documented by Sony.

With further reference to FIG. 3, although not shown it will be understood that the infrared and visible image cameras 54 and 56 are connected to the VDC 52 through suitable cables and connectors, and the videotape recorder 114 is connected to the power interface box 106 or, alternatively, the battery belt 62, through a suitable cable and a connector.

Figure 4:
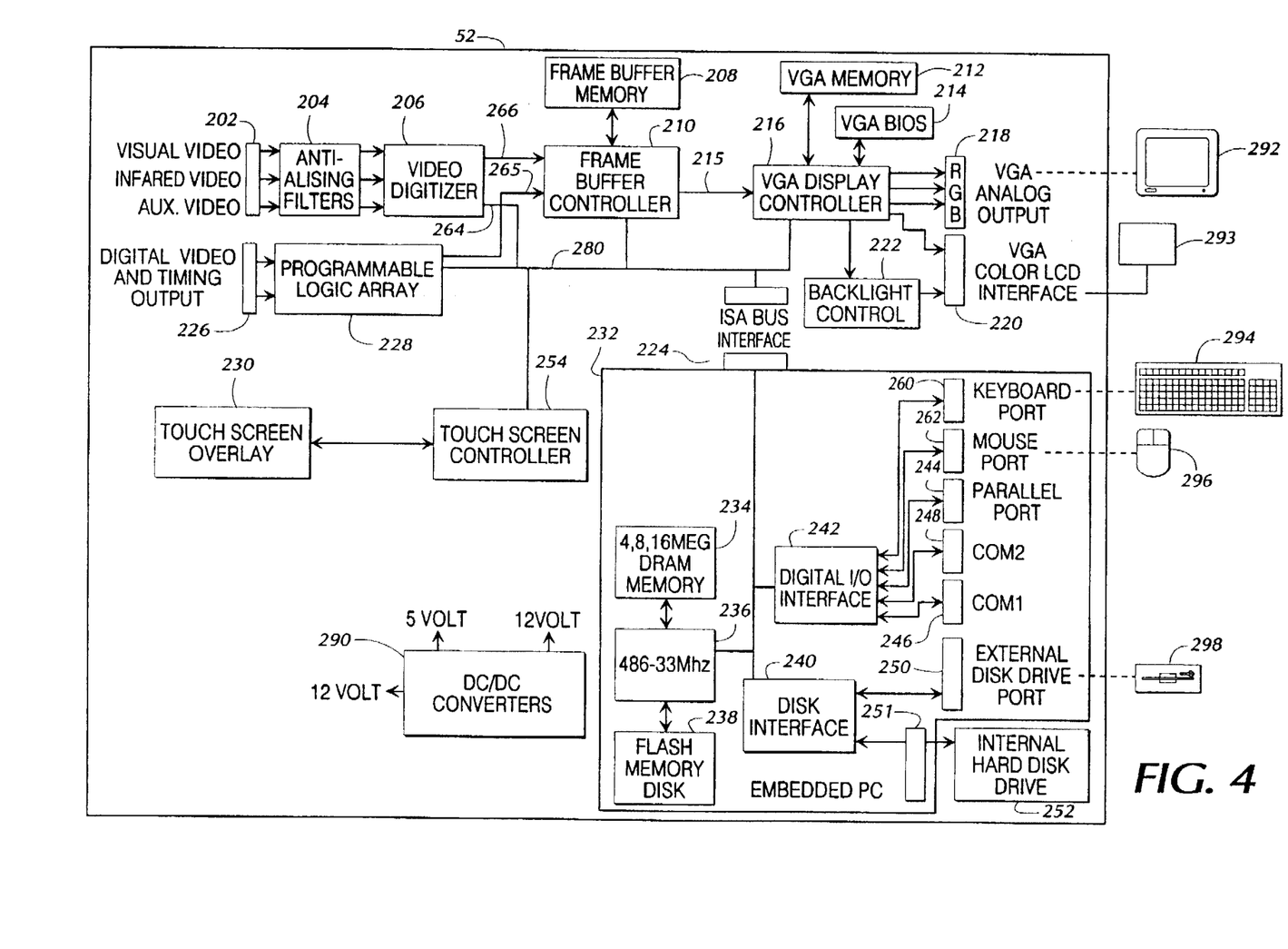
FIG. 4 is a block diagram of the video data collector and its interfaces.

With reference to FIG. 4, the configuration of the VDC 52 will now be described in greater detail. FIG. 4 is a somewhat simplified block diagram of the VDC 52. Power is supplied to the VDC 52 in the form of 12 volt DC power by the battery belt 62 (FIG. 1) and distributed by DC/DC converters 290 in the form of 5 volt and 12 volt regulated power. An internal databus 280, such as an ISA databus, enables data exchange and communication between the various control devices of the VDC 52. An embedded PC 232 is programmable to serve the functions of controlling data exchange on the internal databus 280 as well as recordation of desired images by means of a databus control interface 224.

Although architectural arrangements of the embedded PC 232 may vary without deviating from the intended scope of the invention, the preferred embodiment employs an Intel 486 processor 236 running at a 33 MHz clock speed with Microsoft "WINDOWS" file management software establishing the user interface environment. An embedded PC 232 manufactured by Appcon Group, Inc., part number PCIB-486-4, having a hard disk drive 252 connected by ribbon cable 251 has been found to be particularly suitable for the present invention. DRAM memory 234 provides 4 megabytes of on-board memory, expandable to 16 megabytes. A flash memory disk 238 with 64K bytes of nonvolatile memory enables additional storage for specific power-up applications. Connected to a digital I/O interface 242 are a number of communications and peripheral interface ports including a dedicated keyboard port 260, dedicated mouse port 262, external disk drive port 250, two serial communications ports 246 and 248, and a parallel communications port 244.

Interfaced with the embedded PC 232 by way of a disk interface 240 is an internal hard disk drive 252 of at least 320 megabytes. A disk drive having a large storage capacity is preferred because of the enormous amount of memory required for the storage of infrared and visible images, especially high resolution images. By way of example, thermographic images can have resolutions ranging from 256×192 up to 700×500 and can vary in size from 50K bytes up to 700K bytes.

The embedded PC 232 is generally responsive to commands received from various user interfaces, including a VGA color LCD 293 with touch screen overlay 230, both of which are integral parts of the VDC 52. Handwriting recognition software or popup keyboard residing in the VDC 52 enables the thermographer to enter field notes without a physical keyboard. Peripheral user interfaces include the dedicated keyboard port 260 and the dedicated mouse port 262.

Analog infrared and visible video signals are received from the infrared and visible image cameras 54 and 56 at video signal interface 202. Standard RCA jacks are employed for receiving both visible and infrared analog video. Infrared video signals may be formatted in either NTSC or PAL standards. Visible video signals may be formatted in either NTSC, PAL, or S-video. An auxiliary S-video jack is provided at the video signal interface 202 to support visible video signals formatted in S-video. S-video comprises two separate analog signals, one signal representative of chrominance (color) and the other signal representative of luminance (brightness).

Interface 202 video signals are passed through anti-aliasing filters 204 to eliminate noise. The filtered video signals are then received by video digitizer 206 where they are multiplexed and digitized for output to the internal databus 280 and frame buffer controller 210. In a preferred embodiment, a Brooktree BT812KPF video digitizer with 3 to 1 multiplexing is used. A Chips & Technology F82C9001 controller has been found to be a suitable device for use as a frame buffer controller 210. Two analog video outputs (not shown) are made available to allow for recording to video tape while simultaneously processing images in the VDC 52. One analog video output is a buffered version of the multiplexed video input signal. The other analog video output is a buffered version of the IR video signal only. The video signals are digitized into frames of, for example, 320×200 resolution where each pixel of a frame is represented by a 16-bit Red, Green, Blue (RGB) word having five bits of red, six bits of green, and five bits of blue.

Frame buffer controller 210 receives the digitized video signals from the video digitizer 206 on lines 266 and outputs them to a frame buffer memory 208 and a VGA display controller 216 on lines 215 at rates of at least 30 frames per second. These video images are accessible to the embedded PC 232 through the internal databus 280. Frame buffer memory 208 is essentially a one frame memory device that is constantly being updated with new frames of 16-bit per pixel video data. As each new frame of video data is received, the previous frame immediately is replaced with the new frame so that at any point in time, the frame buffer memory 208 contains only the single most current frame of video data.

Digitized video signals received by the VGA display controller 216, which in a preferred embodiment consists of a Chips & Technology F65535A VGA display controller, are reformatted in accordance with VGA BIOS 214 programming, producing a digital VGA signal which is then stored in VGA memory 212. The digital VGA signal is converted by the VGA display controller 216 from digital to red, green, blue VGA analog signals and made available for display at VGA analog output port 218. The VGA analog signals are also provided to the VGA color LCD 293 for display.

At this point, it should be noted that lines 266 and 215 are particularly useful for enabling video data to be passed along to the frame buffer controller 210 and VGA display controller 216 at high rates of speed, thus eliminating display flicker. These lines 266 and 215 collectively can be viewed as a unidirectional, high speed data bus dedicated to the fast and efficient display of digital video data. By dedicating these lines to passing video data for display only, they enable a marked improvement in efficiency and speed over what would otherwise be realized should video data be communicated exclusively on the internal databus 280.

A function of the VGA display controller 216 is to control switching of the LCD backlight control 222. The LCD backlight (not shown) consumes a great deal of energy relative to the other VDC 52 components. To conserve battery power, the VGA display controller 216 is programmable to switch the backlight off during periods of non-use. For example, time-out settings can be established to turn off the backlight after a defined period of non-use and place the backlight control 222 in an idle mode, so that the backlight is turned on again as soon as a user input is made, such as touching the touch screen overlay 230 or moving a connected mouse 296.

Video signals that are already in digital form may also be received by the VDC 52 and made available to the various controllers 210, 216, and 254, and embedded PC 232, via the internal databus 280. A digital video signal interface 226 provides access to digital video signals from, for example, an infrared camera having a digital output port. The digital video signals are received by a programmable logic array 228 where they are appropriately reformatted and transferred to the frame buffer controller 210 via line 265, stored in frame buffer memory 208 and made available on the internal databus 280. Digital video output formats vary considerably between different manufacturers of infrared cameras. To compensate for these different formats, the programmable logic array 228 is loaded with an appropriate program for converting digital video signals to a standard format that is readily useable by the VDC 52. In the preferred embodiment, programs to compensate for different digital video formats are stored in embedded PC memory 234 and loaded into the programmable logic array 228 by the user through a pop-up menu on the touch screen 230. To maintain flicker free display of digital video data processed by the programmable logic array 228, the processed data is provided to the frame buffer controller 210 on line 265 which sends the data via line 215 at flicker free display rates to the VGA display controller 216.

Video signals may be imaged on either the VGA LCD 293 or the VGA monitor 292, or both simultaneously, in real time at rates of at least thirty frames per second so as to eliminate display flicker. User commands entered through the touch screen overlay 230 are received by a touch screen controller 254 and output to the internal databus 280 where they are made available to the embedded PC 232. A palate of 256 colors is built into the VGA display controller 216. The display controller 216 utilizes "color keying" of this palate to display live video as it is provided to the display controller 216 wherever a keyed color, such as magenta appears. This color keying protocol is stored in VGA memory 212. The display controller 216 will look for magenta pixels in VGA memory 212 and display live video coming in on line 215 at each magenta pixel. In a preferred embodiment, the VGA display controller 216 defaults to magenta on power-up so that live video fills the display 292 or 293 on power-up. This default can be changed by loading VGA memory 212 with a different protocol.

Figure 5:
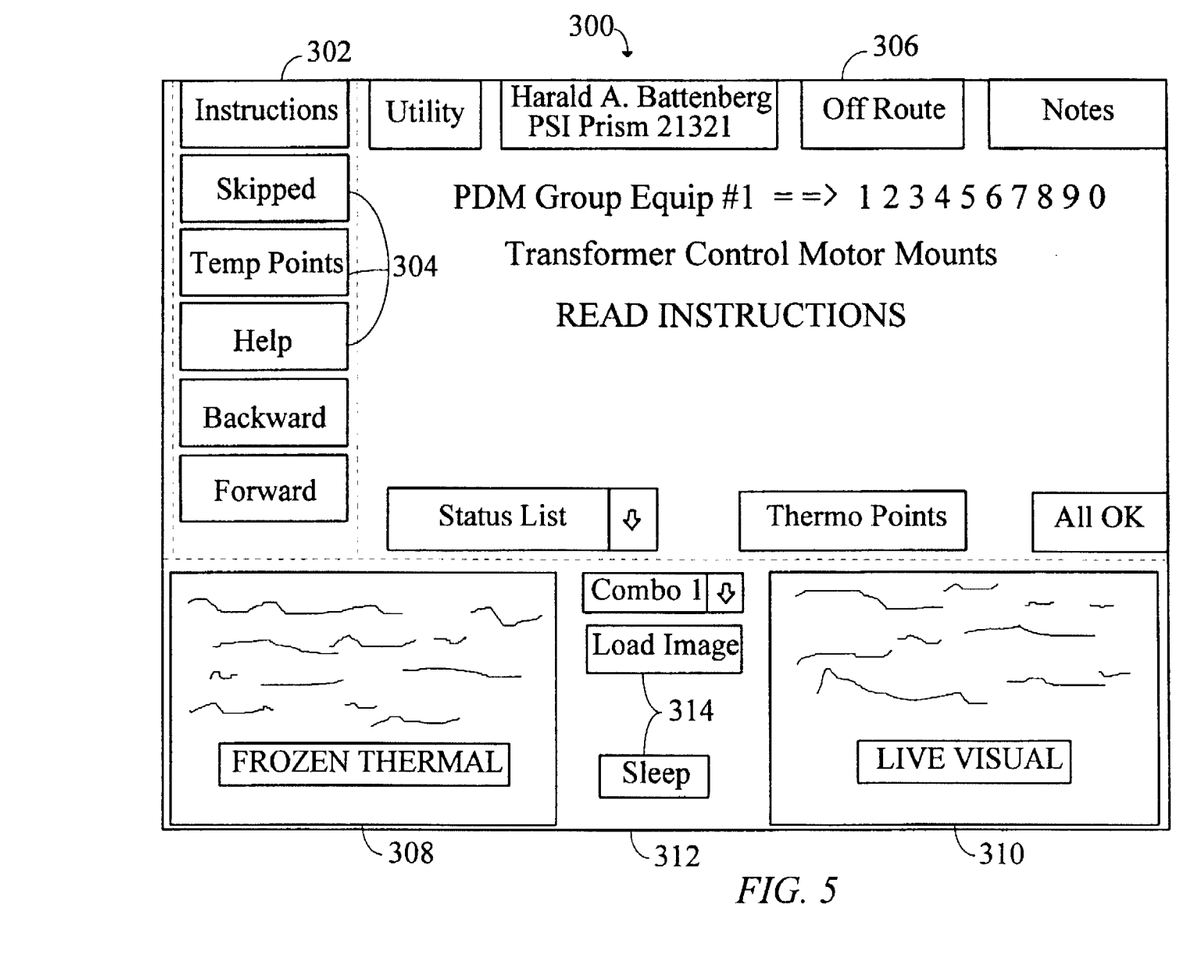
FIG. 5 is an example a user interface screen, with soft keys, which may be displayed on the video data collector to aid in multitasking operations.

FIG. 5 illustrates the format of a VDC user interface screen 300 for performing multiple tasks simultaneously. In a preferred embodiment, the screen 300 is programmed in Visual Basic as a MICROSOFT WINDOWS application. The screen 300 is generally arranged into a number of "zones" containing "soft keys" that allow the user to enter commands by simply touching the soft key area on the screen 300. In this manner, the screen 300 allows the user to conduct thermographic inspections, display live video, freeze images on the screen 300, and conduct other tasks, often simultaneously, without the use of a hardware keypad or mouse. In the upper left hand corner of the screen is a user navigation zone 302 with soft keys 304 for enabling the user to page through a variety of navigation screens that may be called up in the action zone 306, including screens relating to route information, motor control center diagnostics, analysis, report generation, and others.

The user interface screen 300 is formatted to enable simultaneous display of both thermal and visible images. In the lower left hand portion of the screen 300 is a thermal image zone 308 within a video image zone 312. The thermal image zone 308 is dedicated to displaying thermographic images. In the lower right hand portion of the video image zone 312 is a visual image zone 310 dedicated to displaying visual images. Images may be live or frozen in either of the image zones 308, 310. The video image zone 312 includes various soft keys, shown generally at 314, that enable the user to control the displaying of images in either image zone 308, 310, including such functions as freezing images, pulling images from disk, and displaying live video.

The ergonomic advantages of the user interface screen 300 include elimination of hardware keys and other data and command entry devices. A pop-up keyboard enables the user to enter notes and other necessary textual information as required. To display either image zone 308, 310 in full screen format, the thermographer simply touches the image zone and the image currently being displayed converts to full screen size. For example, to display current live video from thermal image zone 308 in full screen format, the thermographer simply touches the screen anywhere within the area of the thermal image zone 308 and the displayed thermal image will immediately fill the screen 300. A single soft key remains available to the user to enable the user to freeze the image in full screen format. The user may touch anywhere on the screen 300 to revert back to the split screen format.

The screen 300 format enables multiple tasks to be performed simultaneously. For example, the user may select to freeze a thermal image of interest in the thermal image zone 308. The frozen thermal image may be visually compared to the live visual image being displayed in the visual image zone 310. Through appropriate softkey entries located in the navigation and action zones 302 and 306, the frozen thermal image may be annotated as described herein while live visual images are being simultaneously displayed. Annotating frozen images while simultaneously displaying live video is exemplary of the many multitasking features enabled by the user interface screen 300.

In field operations, a thermographer will typically first select live infrared video signals for display on the LCD 293 through programmed user prompts on the touch screen overlay 230. Appropriate software is also employed to manipulate captured images before recording, as well as for generating reports that combine images with text. When an image of interest or anomalous condition is displayed and identified by the thermographer, an appropriate command entered via the VDC 52 by the thermographer instructs the embedded PC 232 to freeze the single frame of the image that is currently stored in the frame buffer memory 208. The image on the display 230 will be frozen with the frozen frame being continuously displayed. With entry of an appropriate command on the touch screen overlay 230, the thermographer may then instruct the embedded PC 232 through its programming to save the frozen image to the internal hard drive 252, or the image may be saved to the external disk drive 298 if connected, or both.

Appropriate commands are entered by the thermographer through the touch screen display 230, or if the thermographer desires, a mouse 296 interfaced at mouse port 262 or a keyboard 294 interfaced at keyboard port 260 may be brought into the field to serve as user interfaces. Due to ergonomic restraints and design characteristics, it is anticipated that uses of the keyboard port 260 and mouse port 262, as well as the external disk drive port 250, will be primarily restricted to use with the base station computer 66 of FIG. 1, while the touch screen overlay 230 and LCD 293 will be used primarily when performing thermographic inspections in the field.

Images are stored on either the internal hard drive 252 or external disk drive 298 under a unique base filename that is automatically determined by the embedded PC 232, such as by date and time. The extension is automatically assigned by the embedded PC 232 and is descriptive of the image compression format employed to store the image. To facilitate the subsequent and efficient generation of reports including images, the overall system is capable of generating file formats employing GIF, TIFF, BMT, TGA, PCX, FLI, FLC, CUT, IMG and JPEG image compression formats.

Recorded images are further identifiable by time and date. The time and date at which an image is frozen in the frame buffer is recorded with the image. The recorded time and date will be the time and date at which the image was frozen in the frame buffer, regardless of how long thereafter the image was recorded. Therefore, the time and date at which an image was captured by a camera can be ascertained from the recorded time and date.

It will be appreciated that as part of preventive maintenance measures taken at large industrial facilities or plants, thermographic inspections are typically performed on many different machines and at many different locations of the facility. In addition, a single machine may be thermographically inspected at a variety of different points.

To assist the thermographer who makes a large number of inspections each time he goes out into the field, appropriate software is employed to enable the thermographer to set up an overall framework of the manner in which thermographic inspections will be conducted when monitoring a facility. This framework will be generally referred to as a "route". For example, one aspect of this programmed route consists of templates for entering notes based on visual observations. Handwriting recognition software or a pop up keyboard residing in the embedded PC 236 enables the thermographer to simply write notes into the templates as they are displayed on the LCD 293, thereby eliminating the necessity of a keyboard while in the field. Priority codes for prioritizing repairs are defined, as well as event forms which serve to prompt the thermographer to record all information needed to generate a final report in the event a fault is discovered. Location codes are defined which provide an approach for identifying fault locations on equipment with large dimensions. Instruction codes are defined, attached to particular measurement points, which prompt the thermographer to use proper filters, lenses, distance, angle, and the like. Equipment types found in the plant are defined, such as motor control centers, transformers, pumps, and the like. Components found in the equipment are defined, such as fuses, circuit breakers, insulators, lightening arresters, and the like. There are thermal field observations which the user can pick from a menu or manually enter, including observations such as exceeding normal temperature or an observation of a candy striped thermal pattern indicating that some strands of a wire are making improper or no contact. Fault types which can be associated with the components are defined, and recommended actions that result from particular fault types are defined, thereby enabling the user to conduct diagnostic analyses in the field.

Prior to beginning data collection, route information may be directly input to the VDC 52 via the touch screen overlay 230 or mouse 296 and keyboard 294 peripherals. Alternatively, route information may be defined at the base computer 66 and then uploaded to the VDC 52 via link 67, which is preferably a parallel link.

The thermographer then employs the system 50 in the field to conduct thermographic inspections in accordance with the route. Anomalous conditions (thermographic events), or other events of interest, captured by the infrared camera 54 are recorded on the internal hard drive 252 or the external disk drive 298, along with visible images captured by the visible image camera 56 if desired. Visible images are correlated with thermographic images primarily by filename structure, and secondarily by date and time of capture.

A particularly advantageous feature of the invention enables the thermographer to annotate images of interest in the field. Of course, images may also be annotated at the base computer 66. It should be noted that images may be annotated either prior to recordation on the internal hard drive 252 or external disk drive 298, or subsequent thereto, and both infrared and visible images may be annotated. Following is a description of a preferred method of annotating an image in the field prior to recordation on the hard drive 252.

A live image that has been frozen in the frame buffer memory 208 may be annotated while displayed on the LCD 293. The thermographer uses color keying in combination with the WINDOWS environment to indicate on the LCD 293 the type of annotation he wishes to add, and at what point on the image the annotation should appear. For example, through appropriate commands entered on the touch screen overlay 230 the thermographer may place an arrow at some point on a live infrared image to indicate the presence of a particular anomalous condition. This is done by simply instructing the display controller 216 to draw an arrow at the desired location. An arrow may likewise be annotated onto a captured visible image of the area under observation. As other examples of possible annotations, the thermographer may wish to include text within the image or he may wish to include a small plot of a particular line temperature profile. For annotations with a line temperature profile, the VDC 52 is programmed to derive a line temperature profile from thermographic image data, and to perform a host of other types of analyses, including analyzing average temperature over a defined area, analyzing isotherms, and histograms.

The exemplary arrow, visible image, and line temperature profile annotations are effectively overlayed onto the image as temporary portions of the displayed image. Other annotations may also be overlayed as desired. After all desired annotations are entered, the image (thermal or visual), as it appears on the display 230, can be saved to the hard drive 252 as an image file along with a separate, corresponding annotation file. When a save command is entered, the image frozen in the frame buffer memory 208 is saved to disk as an image file as previously described with the overlayed annotations being saved as a separate .ANN overlay file where the image file and corresponding .ANN overlay files have the same identifying base name. References linking the image and annotation files are stored in an event database, or .EDB file. Multiple faults can also be recorded in the event database. Therefore, there is disclosed an event database, known as the .EDB file, for storing the references to a total of four files associated with each event: (1) A thermal image file, (2) A thermal image annotation file, (3) A visual image file, and (4) A visual image annotation file.

After data collection in accordance with route information is completed, various analyses of the collected data may be performed and reports generated therefrom while the thermographer is still in the field. A portable printer, such as a Canon BJC-600 color bubble jet printer, connected to the appropriate communications port enables the thermographer to print reports as they are generated at each measurement point along the route, thus providing a highly efficient and versatile diagnostic capability. When the system 50 is not in the field performing thermographic inspections and gathering data, it is at times connected to the base station computer 66 of FIG. 1, which is typically a desktop IBM PC, for data transfer between the base station computer 66 and the VDC 52 via link 67. As previously described, the BOGEN quick disconnect is particularly useful when interfacing with the base station computer 66 by enabling the user to quickly and conveniently disconnect the VDC 52 from the vest 60 and then position the VDC 52 on a stand that is capable of enabling the user to adjust viewing angles.

It will be appreciated that although the capabilities of the system 50 of FIG. 1 make it totally independent when deployed in the field—enabling infrared and visible imaging, recording, analysis, and even report generation— the base station computer 66 can be an important tool for the thermographer as well, being complementary to the system 50. For example, the base station computer 66 will typically have a much larger monitor, or display than the VDC 52. The larger VGA monitor 292 typically allows the thermographer to view recorded images with somewhat greater clarity and in greater detail. Also, since the base station computer 66 need not be as portable as the system 50, the thermographer can more easily take advantage of the ergonomic features provided by additional user interfaces such as a mouse and keyboard. And because the base station computer 66 can be much larger than the portable system 50, it can have a much greater data storage capacity than the internal drive 252 of the VDC 52. Therefore, an interface capability with the base station computer 66 is seen as being complementary to, and not a requirement of, the independent nature of the portable system 50.

Accordingly, it will be appreciated that the process of thermographic data collection, annotation, recordation, analysis, and report generation becomes highly automated in a portable system, with a significant reduction in the amount of time required. Comprehensive documentation is produced in the field, including "proof" of inspection at a particular date and time, which can result in a reduction in insurance premiums, depending on the particular plant or facility.

It is contemplated, and will be apparent to those skilled in the art from the foregoing specification and drawings that modifications and/or changes may be made in the embodiments of the invention. Accordingly, it is expressly intended that the foregoing are illustrative of preferred embodiments only, not limiting thereto, and that the true spirit and scope of the present invention be determined by reference to the appended claims.

What is claimed is:

1. A digital infrared thermography system for producing and recording thermographic images of objects, the system comprising:

a portable infrared camera for capturing thermographic images of objects and for producing an electronic thermographic image signal corresponding to said thermographic images;

a digital data processing and recording device for receiving and processing said electronic thermographic image signal to produce a formatted digital signal in the form of a plurality of frames of images, said data processing and recording device including means for performing multiple tasks simultaneously;

digital display means for receiving said formatted digital signal and displaying images corresponding to said formatted digital signal on a first portion of the display while simultaneously displaying on a second portion of the display information allowing a user to perform multiple tasks;

means for selecting individual frames of said formatted digital signal and producing digital frame signals; and digital storage means for storing said digital frame signals.

2. The thermography system as described in claim 1, wherein said digital display means for displaying information to perform multiple tasks comprises means for prompting a user through indications on said display with information selected from the group consisting of location and identification information for equipment to be monitored, and instruction information regarding camera location for particular measurement points.

3. The thermography system as described in claim 1, wherein said digital display means for displaying information to perform multiple tasks comprises means for diagnosing monitored faults.

4. The thermography system as described in claim 1, further comprising a high speed path dedicated to routing the formatted digital signal to said digital display means for display of the formatted digital signal at a rate of at least thirty frames of images per second.

5. The thermography system as described in claim 1, wherein said digital data processing and recording device comprises a video digitizer for digitizing and multiplexing the electronic thermographic image signal to produce the formatted digital signal.

6. The thermography system as described in claim 5, further comprising:

a visible image camera for capturing visible images of objects and for producing an electronic visible image signal corresponding to said visible images; and said video digitizer receiving the electronic visible image signal and digitizing and multiplexing the electronic visible image signal with the electronic thermographic image signal to produce the formatted digital signal.

7. The thermography system as described in claim 6, wherein said visible image camera further comprises an S-video output for providing the electronic visible image signal to said video digitizer in S-video format, said data processing and recording device further comprising an S-video interface for receiving the electronic visible image signal in S-video format.

8. The thermography system as described in claim 6, wherein at least one of said infrared and visible image cameras further comprise a digital output for producing a digital image signal corresponding to captured images, said data processing and recording device further comprising means for receiving and formatting the digital image signal to produce the formatted digital signal.

9. The thermography system as described in claim 8, wherein said means for receiving and formatting comprises a programmable logic array programmable to format the digital image signal for further processing by the data processing and recording device.

10. The thermography system as described in claim 8, further comprising a high speed path dedicated to routing the formatted digital signal to said digital display means for display of the formatted digital signal at a rate of at least thirty frames of images per second.

11. The thermography system as described in claim 1, wherein:
said infrared camera further comprising a digital output for producing a digital thermographic image signal corresponding to said thermographic images;
said data processing and recording device further comprising means for receiving and formatting the digital thermographic image signal to produce the formatted digital signal; and
further comprising a high speed path dedicated to routing the formatted digital signal to said digital display means for display of the formatted digital signal at a rate of at least thirty frames of images per second.

12. The thermography system as described in claim 1, wherein said data processing and recording device maintains a record of identifying information related to stored digital frame signals.

13. The thermography system as described in claim 1, further comprising interface means for interfacing said data processing and recording device to an external computer.

14. The thermography system as described in claim 1, wherein said data processing and recording device is further operable to perform thermographic analyses of the formatted digital signal.

15. The thermography system as described in claim 1, wherein said digital display means comprise a touch screen display.

16. The thermography system as described in claim 1, further comprising a battery for providing power to said system.

17. The thermography system as described in claim 1, further comprising means for supporting on a person's body at least said data processing and recording device.

18. The thermography system as described in claim 17, wherein said means for supporting comprises a carrying vest worn by a user.

19. The thermography system as described in claim 1, further comprising a printer connected to said data processing and recording device for printing at least images.

20. The thermography system as described in claim 1, wherein said data processing and recording device is further operable to allow a user to produce reports.

21. The thermography system as described in claim 1, wherein said data processing and recording device comprises an embedded computer for controlling the processing and display of the formatted digital signal and for controlling the storing of the digital frame signals.

22. The thermography system as described in claim 1, wherein said digital storage means comprise a hard drive internal to said data processing and recording device.

23. The thermography system as described in claim 1, wherein said data processing and recording device is operable to annotate the selected digital frame signals while displayed on the digital display means.

24. A digital infrared thermography unit for processing, displaying, and recording at least thermographic images as represented by thermographic image signals comprising individual frames of thermographic images, said unit comprising:
a camera interface for receiving at least thermographic image signals produced by an infrared camera;
a video digitizer for digitizing and multiplexing image signals received by the camera interface, producing multiplexed image signals;
digital display means for receiving at least thermographic images as represented by said multiplexed image signals;
a high speed path dedicated to routing at least the multiplexed image signals to said display means for display of the multiplexed image signals at a rate of at least thirty frames of images per second;
means for displaying said multiplexed image signals on a first portion of the display while simultaneously displaying on a second portion of the display information allowing a user to perform multiple tasks;
means for selecting individual frames of said multiplexed image signals and producing digital frame signals;
an internal memory for storing said digital frame signals;
an embedded computer for controlling the processing and display of the multiplexed image signal, and for controlling the storage of the selected digital frame signals in said memory; and
a databus interconnecting at least the video digitizer, digital display means, means for selecting, and embedded computer.

25. The thermography system as described in claim 24, wherein said digital display means for displaying information to perform multiple tasks comprises means for prompting a user through indications on said display with information selected from the group consisting of location and identification information for equipment to be monitored, and instruction information regarding camera location for particular measurement points.

26. The thermography system as described in claim 24, wherein said digital display means for displaying information to perform multiple tasks comprises means for diagnosing monitored faults.

27. The thermography unit as described in claim 24, wherein said camera interface is further operable to receive visible image signals produced by a visible image camera.

28. The thermography unit as described in claim 24, wherein said camera interface is further operable to receive visible image signals produced by a visible image camera in S-video format.

29. The thermography unit as described in claim 24, further comprising a digital video signal interface for receiving digital video signals comprised of individual frames of images at a rate of at least thirty frames of images per second.

30. The thermography unit as described in claim 29, further comprising a programmable logic array programmable for converting said digital video signals to a format readily useable by said unit, producing a formatted digital image signal, wherein the formatted digital image signal is received by said high speed path and routed to said display means at a rate of at least thirty frames of images per second.

31. The thermography unit as described in claim 24, wherein said unit is further operable to interface with an external image storage device for at least retrieving stored thermographic images.

32. The thermography unit as described in claim 24, wherein said display means further comprises a touch screen display for accepting user inputs.

33. The thermography unit as described in claim 24, wherein said unit is operable to allow a user to annotate said thermographic images and to record the annotated images.

34. The thermography unit as described in claim 24, wherein said unit maintains a record of identifying information related to recorded images.

35. The thermography unit as described in claim 24, further comprising an external computer interface for communicating data to an external computer.

36. The thermography unit as described in claim 24, wherein said internal memory comprises an internal hard disk.

37. The thermography unit as described in claim 24, further comprising means for supporting said unit on a person.

38. The thermography unit as described in claim 37, wherein said means for supporting said unit comprises a carrying vest worn by a person.

39. The thermography unit as described in claim 37, wherein said means for supporting said unit comprises a hand truck.

40. A digital infrared thermography system for producing, processing, displaying, and recording thermographic and visible images of objects, the system comprising:

a infrared camera for capturing thermographic images of objects and for producing an electronic thermographic image signal comprising individual frames of thermographic images corresponding to the captured thermographic images;

a visible image camera for capturing visible images of objects and for producing an electronic visible image signal comprising individual frames of visible images corresponding to the captured visible images;

a video data collector for receiving, processing, displaying, and recording said thermographic and visible image signals, comprising:

a camera interface connected to said infrared and visible image cameras for receiving said thermographic and visible image signals;

a video digitizer for digitizing and multiplexing the image signals received by said interface, producing multiplexed image signals;

a digital video signal interface for receiving digital video signals comprised of individual frames of images;

a programmable logic array for converting said digital video signals to a format readily useable by said data collector, producing formatted image signals;

a touch screen display for displaying thermographic and visible images as represented by the multiplexed and formatted image signals;

means for selecting and annotating individual frames of the multiplexed and formatted image signals, producing selected digital frame signals;

an internal hard drive for recording the selected digital frame signals; and an embedded computer for controlling the processing and displaying of the multiplexed and formatted image signals, and for controlling the selecting, annotating, and recording of the selected digital frame signals;

a battery for providing power to said system; and a carrying vest for supporting at least said video data collector on a person's body.

* * * * *

UNITED STATES PATENT AND TRADEMARK OFFICE
CERTIFICATE OF CORRECTION

PATENT NO. : 5,637,871

DATED : June 10, 1997

INVENTOR(S) : Kenneth R. Piety, Terry G. Carpenter, Rexford A. Battenberg

It is certified that error appears in the above-indentified patent and that said Letters Patent is hereby corrected as shown below:

In claim 1 at column 14, line 20, after "a", and before "infrared camera", the word "portable" should be deleted.

In claim 24 at column 16, line 41, after "image", the word "signal" should be replaced with --signals--

Signed and Sealed this

Nineteenth Day of August, 1997

Attest:

BRUCE LEHMAN

Attesting Officer

Commissioner of Patents and Trademarks